US006862943B2

(12) United States Patent
Tibbets et al.

(10) Patent No.: US 6,862,943 B2
(45) Date of Patent: Mar. 8, 2005

(54) WATER FILTER MEDIA SAMPLER

(76) Inventors: Michael N. Tibbets, Rte. 1, Box 137, Pattonville, TX (US) 75468; David D. Beard, 3110 Dogwood La., Paris, TX (US) 75460

( * ) Notice: Subject to any disclaimer, the term of this patent is extended or adjusted under 35 U.S.C. 154(b) by 4 days.

(21) Appl. No.: 10/243,806

(22) Filed: Sep. 13, 2002

(65) Prior Publication Data

US 2004/0050185 A1 Mar. 18, 2004

(51) Int. Cl.[7] .................................................. G01N 1/12
(52) U.S. Cl. .................................................... 73/864.64
(58) Field of Search ......................... 73/864.63, 864.51, 73/864.64

(56) References Cited

U.S. PATENT DOCUMENTS

| | | | |
|---|---|---|---|
| 1,256,413 A | | 2/1918 | Wiswell |
| 2,688,877 A | | 9/1954 | Peine .......................... 73/425.2 |
| 2,894,249 A | * | 7/1959 | Flesch ......................... 713/401 |
| 2,968,184 A | | 1/1961 | Archer et al. ............... 73/425.2 |
| 3,080,760 A | | 3/1963 | Piersma ....................... 73/425.2 |
| 3,218,869 A | * | 11/1965 | Fields et al. .............. 73/863.31 |
| 3,596,719 A | * | 8/1971 | Koziski ......................... 175/20 |
| 4,019,380 A | * | 4/1977 | Raymond .................. 73/864.42 |
| 4,088,025 A | | 5/1978 | Foster et al. ................... 73/423 |
| 4,561,315 A | * | 12/1985 | Ontek ....................... 73/864.64 |
| 4,738,142 A | | 4/1988 | Morgan .................... 73/864.64 |
| 4,790,198 A | | 12/1988 | Awtry et al. .............. 73/864.64 |
| 4,804,050 A | | 2/1989 | Kerfoot .......................... 73/20 |
| 4,838,094 A | | 6/1989 | Baldock ................... 73/863.81 |
| 4,866,997 A | * | 9/1989 | Kaufman .................. 73/864.63 |
| 5,179,859 A | | 1/1993 | Van Niekerk ............. 73/864.64 |
| 5,275,245 A | | 1/1994 | Clements ....................... 175/20 |
| 5,337,629 A | | 8/1994 | Kita ......................... 73/864.64 |
| 5,440,941 A | | 8/1995 | Kalidindi ................. 73/864.64 |
| 6,062,093 A | | 5/2000 | Brock et al. .............. 73/864.64 |
| 6,094,999 A | | 8/2000 | DuBois .................... 73/864.64 |

OTHER PUBLICATIONS

Seedburo Equipment Company, *"Grain Probes and Divider"* Brochure, Date and Publication: unknown.
Getting, Thomas M. et al; *"A Practical Guide to Sampling and Testing Filter Media"*, F.B. Leopold Co., Inc., Zelienople, Pennsylvania.
Leopold Water & Wastewater Products; *"Installation, Operation and Maintenance Instructions"*, Nov. 2000.

* cited by examiner

*Primary Examiner*—Charles Garber
(74) *Attorney, Agent, or Firm*—Conley Rose, P.C.; Michael W. Piper; Albert C. Metrailer

(57) ABSTRACT

A sampler for collecting vertically continuous media samples from aggregate liquid filtering systems. The sampler includes a sample collecting lower section have an inner member rotatably carried within an outer member. These lower members have slots which may be aligned by relative rotation of the members. An upper extension section has inner and outer members which are releasably coupled to the lower inner and outer members. The extension section has handles which allow manual rotation of the inner members relative to the outer members. The handles are used to insert the sampler into an aggregate bed, open the slots to collect a sample, close the slots and remove the sampler from the bed.

26 Claims, 2 Drawing Sheets

WATER FILTER MEDIA SAMPLER

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

The present invention relates to sampling of aggregate media in liquid filtration systems and more particularly to apparatus for collecting a vertically continuous sample of media above an underdrain.

Municipal water treatment systems commonly use aggregate filtering systems, commonly referred to as multi-media filters, to remove particulates from water. These filters include multiple layers of aggregate materials in order to efficiently filter water. The bottom of such filters has an underdrain which may be formed of gravel or more modern man made materials, including plastics, rubber, stainless steel, etc. Typical filters have a sand layer immediately above and supported by the underdrain and a layer of anthracite coal particles above and supported by the sand layer. In typical designs, the sand layer is twelve inches thick and the anthracite layer may be eighteen to twenty-four inches thick. More modern regulations require the thicker layer of anthracite. Other filter layers of, for example, greensand or activated carbon may be required depending on the source of water, e.g. well water may contain hydrogen sulfide which can be removed with activated carbon.

The same type of liquid filtration systems may be used for removing particulates from wastewater or process water or other liquids in industrial operations.

In operation, the water or water based fluid to be cleaned flows by gravity down through the aggregate layers of the filter which trap particulates so that clear water flows into the underdrain. After a period of time, the aggregate bed collects enough particulate matter that its flow rate decreases and it must be cleaned. Cleaning is done by backwashing, i.e. flowing clean water into the underdrain and up through the aggregate bed. The upward flow fluidizes the aggregate and flushes the collected particulate matter out of the filter.

In order for an aggregate filter to operate efficiently, the aggregate layers must have certain minimum thicknesses in all areas of the filter. If the backwashing process works properly, the sand, anthracite and others layers naturally arrange themselves in the desired layered arrangement based on particle sizes and specific gravities according to Stokes law. However, the process sometimes does not work for various reasons. One common problem is the formation of mud balls in the aggregate bed. Mud balls are accumulations of coagulants and other deleterious materials that agglomerate in filter media if improper operation of the filter has occurred. Mud balls may have sizes and specific gravities such that they are not removed by backwashing. In other cases, they may simply stick to filter aggregate. In some cases, the underdrain malfunctions and does not uniformly flow water up through the aggregate bed during backwashing. In such cases the bed layers may become unevenly distributed to the extent that the filter does not efficiently remove particulate matter.

During backwashing and during normal operations, small amounts of the filter aggregate materials are commonly lost. If enough of the material, e.g. anthracite, is lost, the aggregate layers will no longer have the minimum required thickness and the filter will not operate as it should.

Filter efficiency is easily measured in terms of the turbidity of the filtered water. If too much particulate matter passes through the filter, the water will not be clear, i.e. it will be turbid. Optical test equipment can measure turbidity of the filtered water on a continuous basis. When the detected turbidity exceeds regulations, it means that the filter has failed and immediate action should be taken to correct the problem.

It is very desirable to monitor the condition of the aggregate layers in water filters so that corrective action can be taken before filter efficiency degrades to an unacceptable point. This is especially true during periods of low water consumption, e.g. winter months, during which times an inefficient filter may provide acceptable filtering due to low flow rate. If the flow rate is increased, e.g. during summer months, the filter may fail to meet turbidity requirements.

Despite the desirability of preventive maintenance monitoring of such filter systems, it is not commonly done due the difficulty of checking the aggregate beds. One common method for checking the condition of water filter aggregate beds requires draining of the filter, insertion of a transparent box into the aggregate bed and manual shoveling out of the materials for measuring layer thicknesses and taking samples for testing. Due to the down time and large labor requirement, this is not normally done until the filtered water fails to meet requirements, i.e. when a failure has occurred.

Attempts have been made to use metal seed samplers such as the grain probes sold by Seedburo Equipment Company of Chicago Ill. to sample aggregate materials used in water filters. During construction of new filtration systems such seed samplers have successfully been used to sample dry anthracite and granular activated carbon from semi-bulk containers. The same seed samplers were not found to be suitable for sampling dry silica gravel, silica sand, high-density gravel and high-density sand in such containers. These hard granular materials cause binding both on opening and closing of the seed sampler.

The seed samplers have a sharp heavy metal point designed to penetrate bulk seed. Such points could easily damage underdrains, especially those made of rubber or plastic. Metal sampling devices also represent a shock hazard in many locations, since the sampling device must be relatively long to be used in typical water filtration systems and must be raised overhead when being inserted into or removed from the filters. The overall length of such seed samplers make them difficult to transport from one location to another. Available seed samplers are of relatively small diameter and have a large number of small openings for collecting seed samples. This opening arrangement interferes with collecting a vertically continuous sample of filter aggregate and interferes with observation, e.g. of transition zones, and measurement of the aggregate layers.

SUMMARY OF THE INVENTION

The present invention provides an liquid filter media sampler having a sample collecting section releasably coupled to an extension section. The sample collecting section includes a first inner tubular member rotatably carried within a first outer tubular member. Each of the first inner and outer tubular members has a slot or elongate opening extending from near a first end to near a second end. The slots substantially match each other and form a valve which can be opened and closed by rotation of the first inner tubular member relative to the first outer tubular member.

The extension section includes a second inner tubular member rotatably carried within a second outer tubular member. The first and second inner tubular members have mating couplings by which they may be coupled together. The first and second outer tubular members have mating couplings by which they may be coupled together.

In one embodiment, each of the second inner and outer tubular members has an attached handle positioned to aid manual handling of the sampler and rotation of the inner tubular members relative to the outer tubular members.

The first outer tubular member has a cap closing its end opposite the releasable coupling. The cap is preferably conical and aids in inserting the sampler into aggregate beds.

In use, the inner tubular members are coupled together and positioned within the first and second outer tubular members. The outer tubular members are then also coupled together. The combined inner tubular members are then rotated so that the slots in the first inner and first outer tubular members are not aligned. The sampler is then lowered into an aggregate filter until the cap is resting on an underdrain. The combined inner tubular members are then rotated so that the slots in the first inner and first outer tubular members are substantially aligned. Aggregate is then allowed to flow through the slot to fill the inner tubular member with a sample of the aggregate layers. The combined inner tubular members are rotated again so that the slots in the first inner and first outer tubular members are not aligned and the aggregate sample is trapped within the sampling section.

The sampler is then removed from the filter and turned to a substantially horizontal position. The combined inner tubular members are rotated again so that the slots in the first inner and first outer tubular members are aligned and the aggregate sample within the sampling section is exposed for observation and removal of samples for testing.

DETAILED DESCRIPTION OF THE INVENTION

Figure 1:
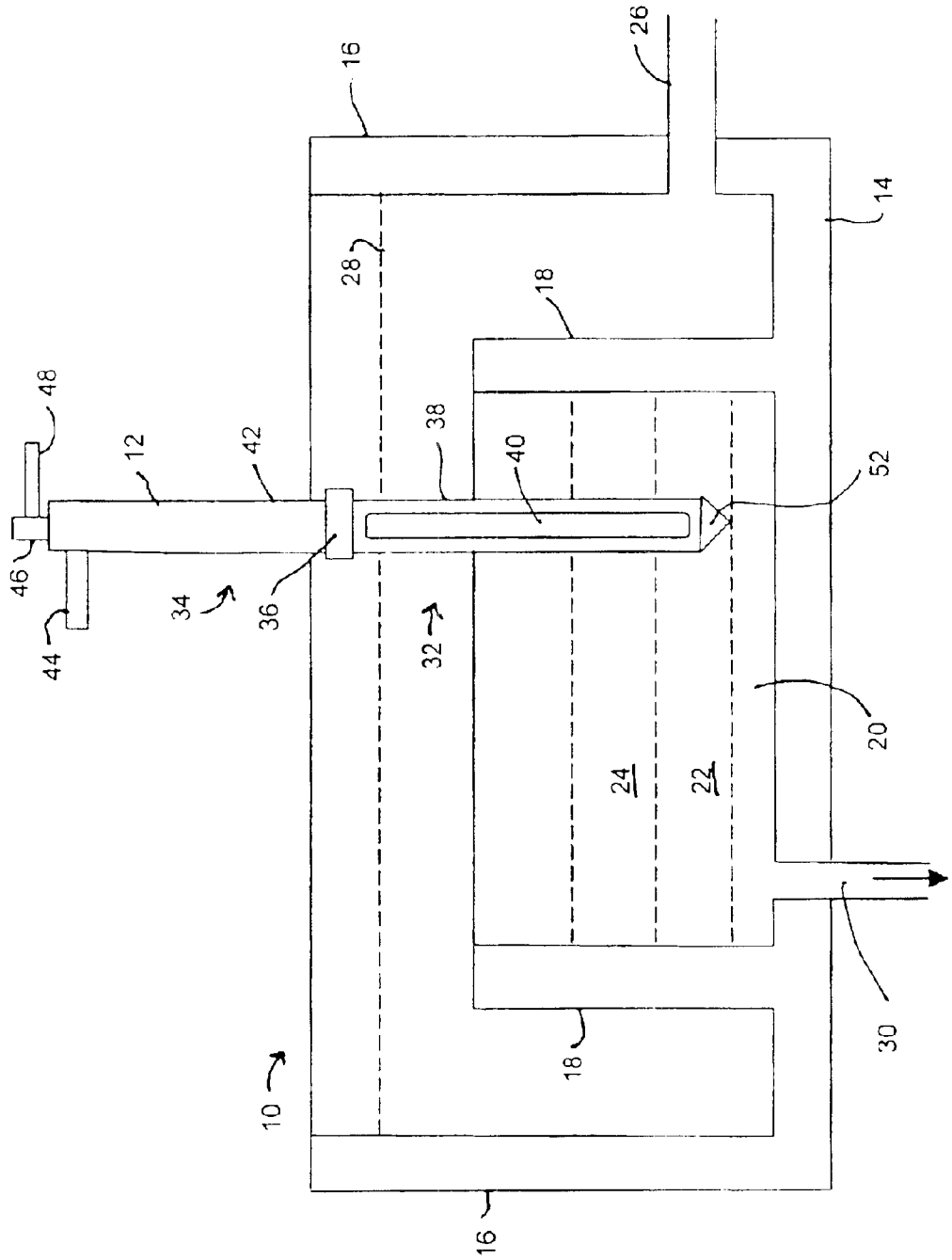
FIG. 1 is a cross sectional view of a typical water filter system with a media sampler according to the present invention inserted for collecting an aggregate sample.

With reference to FIG. 1, the general operation of a typical water filtering system 10 and a media sampler 12 according to the present invention will be described.

The filter system 10 may be in the form of a double trough having a bottom 14, vertical outer walls 16 and vertical inner walls 18. The inner trough defined by walls 18 contain filter elements 20, 22 and 24. Element 20 is an underdrain which may be formed of aggregate, typically gravel, or may be a man made arrangement made of plastic, rubber, stainless steel, etc. On top of underdrain 20 are multiple layers of aggregate filter media. In the most common type of municipal water treatment systems, the underdrain 20 supports a layer of sand 22 on top of which is a layer of anthracite coal 24. The outer walls 16 may have an opening 26 through which water to be filtered may flow into the filter 10. The water may rise to the level indicated by dashed line 28 and flow over the walls 18. The water may then flow down through the filter media layers 24 and 22 and be collected in underdrain 20. The clear water from underdrain 20 may then flow out of opening 30 in the bottom 14 of filter system 10. The flow of water through openings 26 and 30 may be reversed through the underdrain 20 to backwash the filter media 22 and 24. All of these elements of filter system 10 are conventional.

An assembled media sampler 12 according to the present invention is shown in sampling position in FIG. 1. Details of its construction will be described below with reference to FIGS. 2–5. The media sampler 12 is made up of two main parts, a lower sample collecting section 32 and an upper extension and handling section 34. The sections 32 and 34 are releasably connected by couplers, with only coupler 36 for the outer portion of sampler 12 visible in FIG. 1. The lower section 32 includes an outer tubular member 38 having a slot or elongated opening 40 through which filter media may enter the sampler. The upper extension section 34 includes an outer tubular member 42. The members 38 and 42 are connected by releasable coupler 36. On the upper end of member 42 is a handle 44 by which the outer tubular members 38 and 42 may be conveniently lifted and turned. On the lower end of member 38 is a conical cap 52 which closes the lower end and aids in insertion of the sampler 12 down through the media layers 24 and 22.

The terms "upper" and "lower" are used herein to indicate relative positioning of parts when the media sampler 12 is positioned for collecting a media sample as shown in FIG. 1.

An inner tubular member having upper and lower sections is rotatably carried within the outer members 38 and 42. These inner member sections are not visible in FIG. 1 except for the top of upper inner member 46. A handle 48 is preferably attached to this upper end of member 46. The lower section of the inner tubular member has a slot or elongated opening preferably having the same dimensions as opening 40 and thus not separately visible in FIG. 1.

As indicated in the background section above, the filter sand layer 22 should be about twelve inches thick and the anthracite layer 24 should be at least eighteen inches and preferably twenty-four inches thick, in typical filters. The typical total media thickness above underdrain 20 is therefore about two and one-half to three feet. The water level 28 may be four to six feet above the underdrain 20. In the illustrated embodiment, the overall length of sampler 12 is about eight feet, with each section 32 and 34 being about four feet. This size provides a slot 40 at least three feet long which should provide a sample of filter media above underdrain 20 in most currently operating municipal water treatment systems. The overall length places the handles 44 and 48 at a height above the water level 28 and side walls 16 which allows convenient handling and operation of the media sampler 12.

For filters with different dimensions, especially deeper filter media or higher water level, it may be desirable for the length of extender section 34 and sampling section 32 to be adjusted. This can be accomplished simply by using longer parts to make the extender section 34 and the sampling section 32 as appropriate. Alternatively, the extender section 34 may be made of two or more sections coupled together with releasable couplers like coupler 36. Only the top section 34 would have the handles 44 and 48. Intermediate extension sections would have couplers on both ends, to fit between the illustrated sections 34 and 32.

Figure 2:
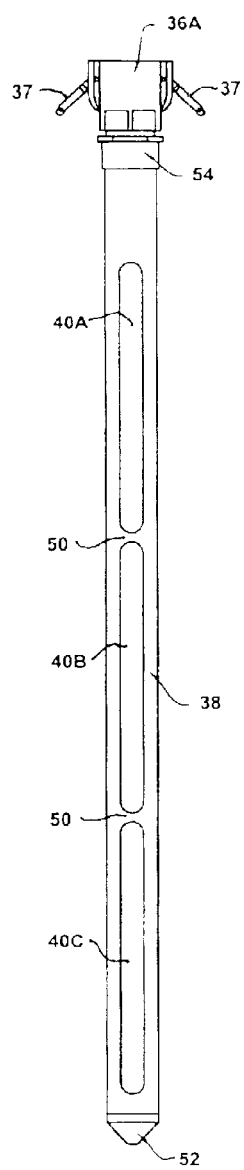
FIG. 2 is an illustration of an outer tubular member portion of a sampling section of a media sampler according to the present invention.

With reference to FIG. 2, details of the lower outer tubular member 38 are shown. In this embodiment, the member 38 is made from a length of nominal two-inch (i.e. about two inch inner diameter and about two and one-quarter inch outer diameter) schedule 40 PVC, polyvinyl chloride, plastic pipe. The slot 40 shown in FIG. 1 is formed of three aligned slots 40A, 40B and 40C having a width of about one to one and one-quarter inch. This arrangement leaves small reinforcing ribs 50, which do not interfere with collection of a representative sample. It is preferred that the ribs 50 not be located at the expected transition zones between filter media layers. For example, for a filter with a twelve inch sand layer, a rib should not be positioned ten to fourteen inches from the bottom of the sampler 12. The lower end of member 38 is sealed by cap or nosepiece 52 also made of PVC. This nosepiece 52 preferably has a conical outer surface which aids in insertion of the sampler into the aggregate layers 22, 24. The total angle of this conical point in this embodiment is about 90 degrees. However, the conical surface has a rounded, instead of a sharp, point so that damage to the underdrain is avoided. Some underdrains are made of rubber or plastic materials, which could be damaged by a sharp endpoint. On the upper end of member 38 is one half 36A of the releasable coupler 36 of FIG. 1. In this embodiment, coupler 36A is the female half of a polypropylene cam lever coupling and is coupled to the member 38 by means of a standard two inch schedule 40 PVC male threaded adapter 54. The nosepiece 52 and adapter 54 are bonded to the member 38 with conventional PVC cement.

As noted above, it is desirable that the ribs 50 not be positioned in transition zones between filter media layers. The sampler 12 may be adapted to various filter configurations by providing additional extenders to position the slots 40A, 40B and 40C at different distances from the bottom of sampler 12. For example, the nose piece 52 can be a removable part, e.g. threaded into member 38, and could be replaced with a six or twelve inch long nose piece to raise the location of slots 40A, 40B and 40C and the ribs 50 above the underdrain. Alternatively extension sections could be inserted between the bottom of member 38 and the nose piece 52. This adjustment can also be made for filters with additional layers or greater than normal overall filter media thickness where it is desired to sample transition zones farther above the underdrain.

Figure 3:
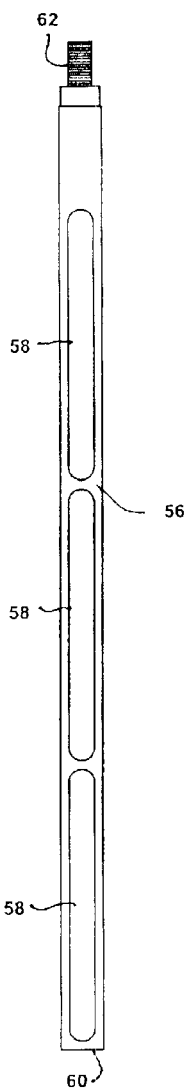
FIG. 3 is an illustration of an inner tubular member portion of a sampling section of a media sampler according to the present invention.

With reference to FIG. 3, the lower inner tubular member 56 is illustrated. In this embodiment, member 56 is manufactured from a length of nominal one and one-half inch (i.e. about one and one-half inner diameter and about one and three-quarter inch outer diameter) schedule 80 PVC pipe. It has slots 58 substantially matching slots 40A, 40B and 40C in the lower outer member 38 (FIG. 2). The lower end 60 of member 56 is left open, but rests on and is effectively sealed by the nosepiece 52 of member 38 when the sampler is assembled. When disassembled, the open lower end 60 facilitates cleaning of the sampler. A threaded coupling 62, is bonded to upper end of member 56. The coupling 62 is made from a solid cylinder of PVC, has a male thread and seals the upper end of member 56.

Figure 4:
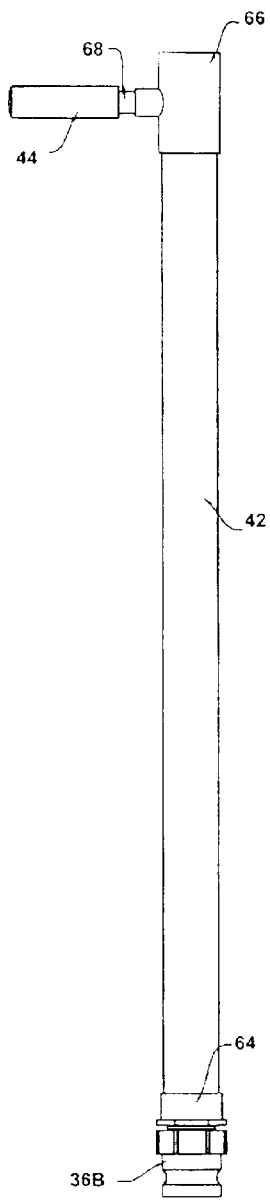
FIG. 4 is an illustration of an outer tubular member portion of an extension section of a media sampler according to the present invention.

With reference to FIG. 4, the upper outer tubular member 42 is illustrated. In this embodiment, the member 42 is made from a length of nominal two inch schedule 40 PVC plastic pipe. On its lower end is a coupling 36B for mating with the coupling 36A on the upper end of member 38. In this embodiment coupler 36B is the male half of a polypropylene cam lever coupling and is coupled to the member 42 by means of a standard two inch schedule 40 PVC male threaded adapter 64. The handle 44 is preferably a slip on rubber handle attached to the upper end of member 42 by means of a two inch by one-half inch schedule 40 PVC tee 66 and a short length of half inch schedule 80 pipe 68.

Figure 5:
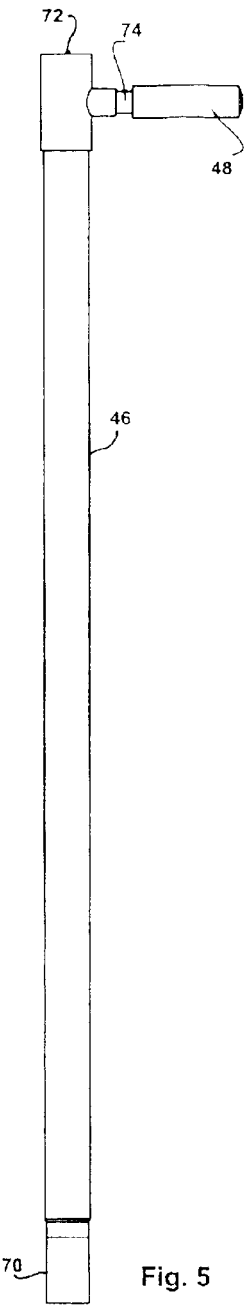
FIG. 5 is an illustration of an inner tubular member portion of an extension section of a media sampler according to the present invention.

With reference to FIG. 5, the upper inner tubular member 46 is illustrated. In this embodiment the member 46 is made from a length of nominal one and one-half inch schedule 80 PVC plastic pipe. On its lower end is a coupling 70 for mating with the coupling 62 on the upper end of member 56. The coupling 70 is made from a solid cylinder of PVC, has a female thread and seals the lower end of member 46. The handle 48 is preferably a slip-on rubber handle attached to the upper end of member 46 by means of a one and one-half inch by one-half inch schedule 40 PVC tee 72 and a short length of half inch schedule 80 pipe 74. The upper inner member 46 is longer than the upper outer member 42, so that the handles 44 and 48 may both be accessible as illustrated in FIG. 1.

The upper inner tubular member 46 need not be a hollow tubular member, i.e. it could be made of a solid cylinder of material. The coupler 70 could then be machined directly into the member 46. The handle 74 could be bonded directly into a hole drilled through the member 46. The preferred embodiment uses a hollow member 46 primarily because it is lighter.

The assembly of the four members illustrated in FIGS. 2–5 will now be described. Note that the media sampler will normally be completely disassembled after each use for cleaning. It will normally not be completely reassembled until it has been transported to a filter system which needs to be sampled, since it is shorter and therefore easier to transport in its disassembled form. Therefore, assembly will normally be required each time the sampler is used. The lower inner member 56 is first inserted most of the way into the lower outer member 38, leaving the coupling 62 exposed. The upper inner member 46 is then inserted all the way into the upper end of the upper outer member 42. The couplers 62 and 70 on the upper and lower inner members 46 and 56 are then threaded together manually. It is preferred to then align the two handles 44 and 48, one directly above the other. The cam lever coupling halves 36A and 36B are then mated, but not locked into place. While making sure that the handles 44 and 48 remain aligned, the lower outer member is rotated until the slots 40 and 58 are aligned. Then the levers 37 on coupling 36 are locked down to latch the upper and lower outer members together.

In view of the above description of the structure and method of assembly of the media sampler 12, it is apparent that various alternative releasable couplers may be used to connect the sampling section 32 to the handling section 34. For example the threaded coupler 70 on the lower end of upper inner member 46 could be formed by a thread in the member 46 itself instead of on a separate part. Couplers for both the inner and outer pairs of members could be splined or keyed so that they fit together in only one orientation to ensure that the relative handle to sampling opening positioning is always the same. Such keyed coupling can be held together with a threaded sleeve as used in pipe joints normally referred to as unions. Non-threaded couplings may also be used.

The particular dimensions of plastic pipe used to make the media sampler 12 are not essential and other sizes may be used if desired. Our experience has indicated that a media sample should be at least one inch in diameter and possibly as large as two inches in diameter. The device described above provides a sample with a diameter of about one and one-half inches, the nominal or inner diameter of the lower inner tubular member. That member could have an inner diameter from one to two inches if desired. The outer tubular member would of course be sized accordingly, i.e. with an inner diameter from about one and one-half inch to about two and one-half inch.

It is also not necessary that the upper inner member be the same diameter as the lower inner member. Likewise, it is not necessary that the lower outer member be the same diameter as the upper outer member. For example, the upper members could have inner diameters corresponding to the outer diameters of the lower members. The lower members could be coupled to the upper members by telescoping part way into the upper members and using pins to lock the parts together.

Use of the media sampler 12 after assembly will be described with reference to FIG. 1. The handles 44 and 48 are rotated out of alignment, preferably on opposite sides of the sampler 12. This takes the slots 40 and 58 out of alignment and closes off the inside of lower inner member 56. The tool is then inserted into the filter system 10 until the nosepiece 52 contacts the top of the underdrain 22. Then the handles 44 and 48 are rotated back into alignment which places the slots 40 and 58 in alignment and allows filter media to flow into the lower inner member 56. It is preferred that the handle 48 be rotated clockwise relative to handle 44 as seen from the top to insure that the threaded coupling between inner members 46 and 56 does not loosen.

Several methods may be used to be sure that the member 56 is filled with an accurate and vertically complete sample of filter media. If the sample is taken during backwashing, the sampler may be left stationary and it will automatically collect a representative sample. The fluidized media will flow through slots 40 and 58 and fill the sampler in the same order it settles in the filter. During normal filter operations, some mechanical movement of the sampler is recommended. The complete tool may be rotated about its axis at least one full rotation by means of the aligned handles 44 and 48. Alternatively, the top of the sampler 12 may be moved in a circular path one or more times causing the sampler 12 to move in a generally conical path through the filter media. Both of these mechanical movement methods have resulted in filling of the sampler with a representative sample.

When the sampler has been filled, the handle 48 is rotated, preferably clockwise, until it is 180° out of alignment with handle 44, and the slots 40 and 58 are out of alignment. The sample is then captured within the sampler. The sampler 12 is then lifted from the filter system 10 and water is allowed to drain from the sampler. Then the tool 12 is laid on a horizontal support with slot 40 facing upward. Handle 48 is then rotated a half turn to bring the slot 58 into alignment with the slot 40 and expose the collected media sample.

With the sample taken and exposed, various measurements and observations may be made and samples may be removed for testing and analysis. The sampler of the present invention provides the important ability to observe the media layers, for example to determine if mud balls are present, and to measure thicknesses. Normally, the interface between sand and anthracite layers occurs over a transition zone of several inches in which the materials are mixed. Some filter designers believe that most filtering takes place in this transition zone and it is important to be sure it exists and has sufficient thickness. The locations and thicknesses of the layers may be measured with a tape measure. In a preferred embodiment, a distance scale is attached to or engraved on the outer surface of member 38 next to slot 40. It indicates distance from the bottom of nosepiece 52. Samples may be scooped from the slot 40 or the sampler 12 may be rolled over on a flat surface to empty out the media sample for collection of samples to be sent for laboratory testing.

After observations and measurements are made and samples collected, the sampler should be disassembled and rinsed to remove filter media. The sampler is then ready to be used again. In most cases, it is desirable to collect a number of samples at different locations in each filter. Nonuniform aggregate layers or ineffective backwashing, indicated for example by the presence of mud balls, can be visually identified. The visual inspection of the media can indicate where problems such as clogged underdrain portions or deficient media thickness exist. The ability to quickly take multiple representative samples of media from a liquid filtration system is an important advantage of the present invention. The ability to take samples during normal operation of a filter is also an important advantage. These advantages make it practical to perform the sampling procedure on a regular preventive maintenance schedule.

While the media sampler of the present invention could be made from other materials, the plastics used in the preferred embodiments have a number of advantages. From a regulatory standpoint, PVC plastic is generally approved for public drinking water systems. It is non-conductive, and avoids possible shock hazards, which can occur due to accidental contact with lighting fixtures over filter systems or contact with electrodes, which are commonly used for water level control in filters. Additionally, plastic is lighter than metals and will not rust or corrode. While the PVC materials described herein are most preferred, other plastic materials may also be used. In any case, non-conductive materials are preferred. It is believed that the relative softness or malleability of plastics makes them more suitable than metal for sampling the aggregate materials, since they do not exhibit the binding which occurred when a metal seed sampler was tested.

The present inventors attempted to use the Seedburo grain probe discussed in the background section to collect a media sample in a working water filter. Several problems were encountered. The wet aggregate materials, sand and anthracite, caused some binding making the device difficult to operate. The small openings which are widely separated made it difficult to collect a representative sample and to visually inspect the sample which was collected. The fact that it is made of metal presented the electrical shock risks discussed above. Its overall length made it difficult to transport to the location of water filters.

While the present invention has been described with reference to water filtration systems with two media layers, sand and anthracite, it is equally useful with filtration systems with different or additional media layers. It is also useful with liquid filtration systems used for removing particulates from wastewater or process water or other liquids in industrial operations. As noted above, layers of activated carbon or greensand are sometimes required if the liquid being filtered contains certain undesirable materials or odors. If deeper filter beds are used, the dimensions of the media sampler 12 can be changed to take a representative sample of all layers. Additional extender sections may be provided above or below the sampling section to reach a targeted region for sampling.

While the present invention has been illustrated and described in terms of particular apparatus and methods of use, it is apparent that equivalent parts may be substituted for those shown and other changes can be made within the scope of the present invention as defined by the appended claims.

What we claim as our invention is:

1. A liquid filter media sampler, comprising:
   a sample collecting section comprising a first outer tubular member and a first inner tubular member, said first inner tubular member rotatably carried within said first outer tubular member, each of said first outer and first inner tubular members having a first end and a second end and having an elongate opening parallel to a line extending from a point near said first end to a point near said second end, the inner tubular member defining a continuous media sample chamber having a length selected to collect a vertically continuous media sample through at least a transition zone of the filter media,
   a cap closing said first end of said first outer tubular member and rotatably supporting the inner tubular member,
   a coupler on the second end of each of said first inner and first outer tubular members,
   a first extension section comprising a second outer tubular member and a second inner tubular member, said second inner tubular member rotatably carried within said second outer tubular member, each of said second outer and second inner tubular members having a first end and a second end,
   a handle coupled to the second end of said second outer tubular member,
   a coupler on the first end of said second inner tubular member and adapted for releasable engagement with said coupler on the second end of said first inner tubular member, and
   a coupler on the first end of said second outer tubular member and adapted for releasable engagement with said coupler on the second end of said first outer tubular member,
   said coupler on the second end of said first outer tubular member and the coupler on the first end of said second outer tubular member comprising mating portions of a cam lever coupling adapted to couple said first outer tubular member to said second outer tubular member at any relative angular orientation to permit alignment of the handle attached to the second outer tubular member relative to the elongate opening of the first inner tubular member, and prevent relative rotation of said outer tubular members after coupling.

2. A liquid filter media sampler according to claim 1, further comprising:
   a handle coupled to the second end of said second inner tubular member.

3. A liquid filter media sampler according to claim 2, wherein:
   said handles are positioned at substantially right angles to said second outer tubular member and said second inner tubular member.

4. A liquid filter media sampler according to claim 1, wherein:
   said first inner tubular member, said first outer tubular member, said second inner tubular member and said second outer tubular member each comprise a length of plastic pipe.

5. A liquid filter media sampler according to claim 4, wherein:
   said plastic pipe comprises polyvinyl chloride.

6. A liquid filter media sampler according to claim 1, wherein:
   said coupler on the second end of said first inner tubular member and the coupling means on the first end of said second inner tubular member comprise mating threaded surfaces.

7. A liquid filter media sampler according to claim 1, wherein:
   said elongate opening in said first inner tubular member and said elongate opening in said first outer tubular member comprises two or more elongate openings aligned end to end along the length of said first inner tubular member and said first outer tubular member.

8. A liquid filter media sampler according to claim 1, wherein:
   each of said sample collecting section and said first extension section is about four feet long.

9. A liquid filter media sampler according to claim 1, wherein:
   said first and second outer tubular members each have an inner diameter of between about one and one-half inches and about two and one-half inches and said first and second inner tubular members have an inner diameter of between about one and about two inches.

10. A liquid filter media sampler according to claim 1, wherein:
    said first and second outer tubular members each have an inner diameter of about two inches and said first and second inner tubular members have an inner diameter of about one and one-half inch.

11. A liquid filter media sampler according to claim 1, wherein:
    said cap comprises a conical outer surface.

12. A liquid filter media sampler according to claim 11, wherein:
    said conical outer surface comprises a rounded point.

13. A liquid filter media sampler according to claim 1, wherein:
    said cap defines the lowermost point of said sampler, and said cap has a length selected to position the elongate openings a preselected distance above the lowermost point of said sampler.

14. A liquid filter media sampler according to claim 1, wherein:
    said first inner tubular member has a diameter about the same as the diameter of said second inner tubular member, and
    said first outer tubular member has a diameter about the same as the diameter of said second outer tubular member.

15. A liquid filter media sampler according to claim 1, further comprising:
    a second extension section comprising a third inner tubular member rotatably carried within a third outer tubular member, each of said tubular members having couplers on both ends adapted to couple said second extension section between said first extension section and said sample collecting section.

16. A liquid filter media sampler according to claim 1, wherein the media sample chamber has a length selected to collect a vertically continuous media sample through substantially the whole depth of a filter media.

17. A liquid filter media sampler according to claim 1, wherein the media sample chamber has a length selected to collect a vertically continuous media sample through a depth range including the location of a filter media transition zone during filter backwashing.

18. A liquid filter media sampler according to claim 1, wherein: said first and second outer tubular members each have an inner diameter of about two inches and said first and second inner tubular members have an inner diameter of about one and one-half inch.

19. A liquid filter media sampler, comprising:
   a sample collecting section comprising a first outer tubular member and a first inner tubular member, said first inner tubular member rotatably carried within said first outer tubular member, said first inner tubular member and first outer tubular member having a common central axis, each of said first outer and first inner tubular members having a first end and a second end and having an elongate opening parallel to a line extending from a point near said first end to a point near said second end, the inner tubular member defining a continuous media sample chamber having a length selected to collect a vertically continuous media sample through at least a transition zone of the filter media, and
   a cap closing said first end of said first outer tubular member and rotatably supporting the first inner tubular member first end,
   the dimension of the first inner tubular member and first outer tubular members selected to allow liquid to flow from the first inner tubular member elongate opening, between the first inner tubular member and first outer tubular member and out the first outer tubular member elongate opening, but to substantially restrict the flow of filter media between the first inner tubular member and first outer tubular member, when the first inner tubular member elongate opening and first outer tubular member elongate opening are not aligned.

20. A liquid filter media sampler according to claim 19, wherein the first inner tubular member first end has an opening and is supported on the cap with a fit that allows liquid to flow out of the first inner tubular member, but substantially restricts the flow of filter media from the first inner tubular member.

21. A liquid filter media sampler according to claim 20, wherein: said first inner tubular member, said first outer tubular member, said second inner tubular member, and said second outer tubular member each comprise a length of plastic pipe.

22. A liquid filter media sampler according to claim 19, further comprising:
   a coupler on the second end of each of said first inner and first outer tubular members,
   a first extension section comprising a second outer tubular member and a second inner tubular member, said second inner tubular member rotatably carried within said second outer tubular member, each of said second outer and second inner tubular members having a first end and a second end,
   a coupler on the first end of said second inner tubular member and adapted for releasable engagement with said coupler on the second end of said first inner tubular member, and
   a coupler on the first end of said second outer tubular member and adapted for releasable engagement with said coupler on the second end of said first outer tubular member.

23. A liquid filter media sampler according to claim 19, wherein the media sample chamber has a length selected to collect a vertically continuous media sample through substantially the whole depth of a filter media.

24. A liquid filter media sampler according to claim 19, wherein the media sample chamber has a length selected to collect a vertically continuous media sample through a depth range including the location of a filter media transition zone during filter backwashing.

25. A liquid filter media sampler according to claim 19, wherein: said elongate opening in said first inner tubular member and said elongate opening in said first outer tubular member comprises two or more elongate openings aligned end to end along the length of said first inner tubular member and said first outer tubular member.

26. A liquid filter media sampler according to claim 19, wherein: said cap defines the lowermost point of said sampler, and said cap has a length selected to position the elongate openings a preselected distance above the lowermost point of said sampler.

* * * * *